United States Patent
Nicholson

(10) Patent No.: US 7,677,887 B2
(45) Date of Patent: Mar. 16, 2010

(54) SHAPE MEMORY SELF-LIGATING ORTHODONTIC BRACKETS

(76) Inventor: James A. Nicholson, 120 S. 28th Ave., Hattiesburg, MS (US) 39401

(*) Notice: Subject to any disclaimer, the term of this patent is extended or adjusted under 35 U.S.C. 154(b) by 187 days.

(21) Appl. No.: 10/882,193

(22) Filed: Jul. 2, 2004

(65) Prior Publication Data

US 2006/0003282 A1    Jan. 5, 2006

(51) Int. Cl.
*A61D 3/00* (2006.01)
(52) U.S. Cl. ............................. 433/11; 433/8
(58) Field of Classification Search .............. 433/8, 433/9, 10, 11, 12, 13, 14, 15, 16, 17
See application file for complete search history.

(56) References Cited

U.S. PATENT DOCUMENTS

| | | | |
|---|---|---|---|
| 3,084,437 A | 4/1963 | Neger | |
| 3,327,393 A | 6/1967 | Brader | |
| 3,464,112 A | 9/1969 | Silverman | |
| 3,855,701 A | 12/1974 | LeClair | |
| 4,299,569 A * | 11/1981 | Frantz | 433/8 |
| 4,954,080 A | 9/1990 | Kelly et al. | |
| 5,059,119 A * | 10/1991 | Snead | 433/17 |
| 5,094,614 A * | 3/1992 | Wildman | 433/14 |
| 5,232,361 A | 8/1993 | Sachdeva | |
| 5,356,288 A * | 10/1994 | Cohen | 433/8 |
| 5,356,289 A | 10/1994 | Watanabe | |
| 5,358,402 A | 10/1994 | Reed et al. | |
| 5,380,196 A | 1/1995 | Kelly et al. | |
| 5,429,499 A * | 7/1995 | Sernetz | 433/8 |
| 5,439,379 A | 8/1995 | Hansen | |
| 6,267,590 B1 * | 7/2001 | Barry et al. | 433/8 |
| 6,302,688 B1 | 10/2001 | Jordan et al. | |
| 6,305,932 B1 * | 10/2001 | Mottate | 433/8 |
| 6,509,094 B1 * | 1/2003 | Shah et al. | 428/395 |
| 6,554,612 B2 | 4/2003 | Georgakis | |
| 6,582,226 B2 | 6/2003 | Jordan et al. | |
| 6,663,385 B2 | 12/2003 | Tepper | |
| 6,695,612 B2 * | 2/2004 | Abels et al. | 433/10 |
| 6,733,286 B2 * | 5/2004 | Abels et al. | 433/11 |
| 6,932,597 B2 * | 8/2005 | Abels et al. | 433/10 |
| 2001/0029008 A1 * | 10/2001 | Jordan et al. | 433/10 |
| 2005/0260532 A1 * | 11/2005 | Feller | 433/2 |

OTHER PUBLICATIONS photograph and packaging label of SmartClip™ by 3M Unitek, Monrovia CA 91016 (2004).

* cited by examiner

*Primary Examiner*—Cris L Rodriguez
*Assistant Examiner*—Hao D Mai
(74) *Attorney, Agent, or Firm*—Dowell & Dowell, P.C.

(57) ABSTRACT

Self-ligating orthodontic brackets with archwire retainers formed of materials exhibiting shape memory. Each bracket which includes a base from which extends two spaced and opposing pairs of tie wings each pair of which define an archwire guide slot therebetween. The retainers include at least one flange to retain an archwire within the archwire guide slot but which is yieldable to permit insertion and/or removal of the archwire relative to the archwire guide slots. Portions of the brackets and/or retainer may be coated to reduce friction between the archwire and the bracket and to promote aesthetics and overall bracket appearance.

18 Claims, 5 Drawing Sheets

SHAPE MEMORY SELF-LIGATING ORTHODONTIC BRACKETS

BACKGROUND OF THE INVENTION

1. Field of the Invention

This invention is generally directed to orthodontic brackets for use in aligning teeth and more specifically to self-ligating orthodontic brackets that use shape memory metallic alloy or non-metallic resin or polymer archwire slot retainers, including inserts and/or retainer flanges, that may be inserted and welded or otherwise attached to metallic or non-metallic brackets which include two pair of opposing tie wings which are spaced relative to one another to define archwire slots therebetween. The retainers serve to selectively and guidingly receive and retain an archwire within the archwire guide slots defined by each pair of opposing tie wings.

2. Brief Description of Related Art

Generally, there are two basic styles of orthodontic brackets. A first style is known as a single wing wherein a pair of opposing elongated tie wings extend upwardly from a bracket base and are spaced to define an archwire guide slot therebetween. An example of a self-ligating single wing style bracket is disclosed in U.S. Pat. No. 6,663,385 to Tepper.

Twin brackets are the second style of brackets and have been developed to increase ease of bracket placement and use. Twin brackets include two pair of opposing tie wings which are spaced from one another with each pair defining an archwire guide slot therebetween. An example of such a bracket is described in U.S. Pat. No. 5,232,361 to Sachdeva et al. wherein the brackets are formed of titanium so as to be very hard and rigid. An example teaching away from a spaced pair of tie wings is disclosed in U.S. Pat. No. 5,356,289 to Watanabe wherein the brackets are formed of shape memory alloys or resins.

A variation of the twin bracket style has been developed to make the twin brackets self-ligating in order to avoid the necessity to tie-off the archwire used with the brackets. Such self-ligating twin brackets use supplemental hooks or latches which are mounted adjacent to each pair of tie wings for securely engaging or clamping an archwire. Unfortunately, the additional structure not only increases bracket costs and size, but also decreases bracket aesthetics and provides additional structure for trapping food and bacteria. An example of such a bracket is described in U.S. Pat. No. 6,554,612 to Georgakis et al.

Orthodontists are faced with many treatment difficulties as they bond orthodontic brackets to a patient's teeth and move them from crooked and irregular malocclusion positions to their ideal positions. The ideal alignment of teeth demands that they must be straight and aesthetical pleasing, but the teeth must also fit together correctly into normal occlusion and look and function in a superior clinical manner. There are a number of major challenges that Orthodontists must overcome to produce this superior clinical result.

There is often limited access to areas of the teeth where brackets must be placed to achieve normal orthodontic movement and produce superior treatment results. Useful areas may be small with access thereto very restricted, in which case, large brackets are not used successfully; whereas, smaller and compact twin type brackets can be placed in small areas and have enjoyed exceptional popularity among Orthodontists.

Ideal bracket placement on a patient's teeth is also necessary to produce ideal tooth alignment and achieve exceptional orthodontic results. To accomplish this necessary goal of ideal placement, brackets must often fit into small spaces between crooked and rotated teeth. A design feature of having a recessed point or horizontal groove located in the approximate center of the bracket will permit an Orthodontist to use a measuring device, such as a Boone Gauge, to precisely position brackets on teeth in exact desired positions.

Complete archwire engagement of the brackets on the teeth during various stages of orthodontic treatment is important but may not be possible. Many times, due to crooked alignment and closeness of the teeth, only two of the four bracket tie wings can be engaged at the same time. With single wing brackets or brackets without tie wings, it is extremely difficult to accomplish partial engagement successfully and this can result in an uncontrolled and unsatisfactory tooth movement. The true twin bracket design permits the engagement of at lease two of the opposing bracket tie wings to be used to begin tooth movement and, later in the treatment, two pair of opposing bracket tie wings can be used without compromising the patient's treatment.

The tooth movement process that is required to straighten teeth is very dynamic and constantly changing. The Orthodontist must have brackets that will accommodate the dynamics of tooth movement and not require replacement with new ones when a certain movement is required due to the difficulty of the patient's case.

Attachments such as Kobayashi hooks, metal ligatures, directional force elastics, elastomeric ties or elastomeric power chains are often used during various stages of orthodontic treatment. It is difficult to place such attachments on single wing style brackets and extremely difficult to place them on brackets without tie wings, however, a twin bracket configuration having four tie wings permits the Orthodontist to easily place such attachments and satisfactorily accomplish different aspects of a treatment.

Friction occurs as a normal part of tooth movement as a bracket and tooth slide along an archwire. This process is know as the sliding mechanics of orthodontics. The more points of contact between the archwire and a bracket slot during this process the greater the friction, which results in slower tooth movement and makes the treatment take longer. Elongated single wing brackets have increased friction resisting tooth movement and thus treatment is lengthy and more complicated to complete.

The aesthetic demands of the orthodontic patient are many and must be addressed to make the treatment acceptable to the patient. The larger single wing brackets are not aesthetically pleasing, but are the smaller metal twin brackets are an improvement. The ceramic and non-metallic brackets are much improved aesthetically but neither the smaller metal twin brackets or the non-metallic ceramic offer a true twin self-ligating design.

Another major challenge of orthodontic treatment is the cleanliness of the brackets and areas where they are bonded or banded to the teeth. It is difficult for patients to clean areas adjacent to brackets and tooth surfaces. Bracket elements function as plaque traps that increase the chance of permanent stains, tooth decay, and gum disease. The use of larger single wings brackets makes it much harder for patients to keep their braces clean. The smaller twin designs are much easier for patients to clean and thus greatly reduced trapped food and are less likely to cause stains, tooth decay, or gum disease.

During the course of orthodontic treatment, archwires are placed and removed from the bracket/bracket slot as a normal part of treatment. Since most orthodontic brackets are made of stainless steel, both the bracket and bracket slots are rigid and inflexible. Once the archwire is placed in the bracket slot, it must be tied or ligated in place to prevent the archwire from coming out of the bracket and injuring the patient. The process of tying and untying every bracket to secure the archwire is a tedious and laborious procedure that must be repeated each time a new archwire is placed or removed. This process is time consuming and uncomfortable for the patient and inefficient for the Orthodontist. Self-ligating brackets have the advantage of using various mechanisms to secure archwires in the bracket slots without the need for metal or elastic ligatures. Because the current self-ligating brackets on the market are not a true twin bracket design, they have serious limitations such that they are bulky and cumbersome to use in the small confines of the oral cavity.

In the 1980's nickel-titanium was introduced to orthodontics in the form of archwires with the trademark name of Nitinol™. The flexibility, shape memory effect, and superelasticity of Nitinol™ archwires offered a new wire that could be deflected to engage misaligned teeth and would return to its original form thereby straightening the teeth. The flexibility, shape memory effect, and superelastic nickel-titanium material has not, however, been used to construct a true twin bracket that looks and is shaped like the traditional stainless steel twin brackets.

SUMMARY OF THE INVENTION

This invention is directed to orthodontic brackets of the twin tie wing style wherein each bracket includes a base from which extends two pair of opposing tie wings. Each tie wing includes a post and a head portion with each pair of opposing posts defining an archwire guide slot therebetween of a dimension between approximately 0.018" to 0.022" to slidingly receive an archwire. The head portions include oppositely oriented outwardly extending flanges which may be used in a conventional manner for use in securing archwires with ligating wires or adding other attachments which may be required during a patient's treatment.

In the present invention, one or more archwire retainers formed of a shape memory metallic alloy or non-metallic resin or polymer type materials that include nickel-titanium alloy material are secured or otherwise mounted in each archwire slot for purposes of retaining an archwire relative to the orthodontic bracket. Each retainer includes at least one flange which exhibits some degree of flexibility and shape memory such that the flange may be flexed to permit insertion and removal of an archwire relative to the archwire slots. In some embodiments the inserts include opposing flanges which may be flexed such that they separate to a distance to permit the insertion and/or removal of an archwire relative to the archwire guide slots defined between the tie wings, afterwhich the flanges return to a predetermined position.

The two pair of opposing tie wings are spaced from one another and extend from the front surface of the bracket base such that the archwire slots are generally axially aligned relative to one another. In preferred embodiments of the invention, either a recessed point or horizontal groove is provided at or along the approximate center of each bracket base for purposes of precision alignment of the bracket with respect to a tooth using an instrument such as Boone gauge.

In a first embodiment, the archwire retainers are formed having generally U-shaped bodies with spaced generally parallel leg members extending upwardly from a base. The upper or free end of at least one of the legs includes a flange portion which extends toward the opposing leg to such an extent that an archwire seated between the legs can not be removed from the retainer without moving the at least one flange to create a space through which the archwire may pass. In some embodiments, opposing flanges extend toward one another from each leg of the retainer.

The at least one flange and/or the leg associated therein are formed of a shape memory material as described herein, such that the leg and/or the flanges may be flexed from a predetermined position and thereafter return to the predetermined position, whereby the leg and/or the at least one flange are used to retain an archwire in an archwire slot defined by a pair of opposing tie wings.

In another embodiment, the retainer is formed in a generally L-shape configuration wherein one leg of the body is designed to be welded or otherwise secured to a post of a tie wing while the other leg functions as a retainer flange as described with respect to the previous embodiment. At least the leg functioning as the retainer flange is formed of a material exhibiting shape memory.

The retainer may also be designed to be seated within archwire slot defined between a single pair of tie wings, or may be elongated so as to seated between two pair of opposing tie wings.

To reduce friction between an archwire and the orthodontic brackets of the present invention, the brackets, and/or archwire retainers, except the bonding mesh pads of the brackets, may be coated with a polytetrafluoroethylene (PTFE) material such as Teflon™, thermosetting polymer or other polymeric coatings with or without a coupling agent which form a smooth surface between the bracket and an archwire. To promote adherence of the coating, the brackets may be physically treated such as by a blasting process, chemical etching or the like. Archwires associated with the brackets and/or archwire slot inserts and flanges of the present invention may also be similarly coated.

As opposed to plastic or polymer coatings, the brackets and/or archwire retainers may be plated or electroplated with a metallic material such as nickel, gold, copper or silver in order to reduce friction of the surface to promote sliding of an archwire relative to the brackets during patient treatment and/or to enhance aesthetics.

It is a primary object of the present invention to provide orthodontic brackets which are self-ligating and which have archwire retainers in the form of inserts or flanges that are formed of a shape memory metallic alloy or non-metallic resin or polymer type material, including nickel-titanium materials. The shape memory or nickel-titanium type materials allow the archwire retainers of the brackets to exhibit super-elasticity and shape memory such that portions thereof may be flexed to permit insertion and removal of an archwire relative to the archwire guide slots and thereafter immediately recover to their predetermined configuration and position to retain the archwire in the archwire guide slots between each pair of tie wings.

It is also an object of the invention to provide self-ligating orthodontic brackets which include archwire retainers having at least one flange which exhibits shape memory and which extends from one of each pair of opposing tie wings of the brackets so as to normally retain an archwire within archwire guide slots defined between the opposing pairs of tie wings but which flanges may be moved on flexed to permit insertion and withdrawal of the archwire relative to the archwire guide slots and thereafter recover to an initial predetermined position. In some embodiments, such flanges may extend toward one another from opposing tie wings.

It is another object of the present invention to provide twin tie wing styled orthodontic brackets which include two pair of opposing tie wings each of which defines an archwire guide slot therebetween and wherein the pairs of tie wings are spaced relative to one another such that the brackets may be used in their position for initial treatment wherein an archwire may only pass between one pair of tie wings and thereafter may be adjusted such that the archwire passes through the archwire guide slots between both pair of tie wings as treatment progresses.

It is yet a further object of the present invention to provide nickel-titanium or other shape memory type archwire retainers for orthodontic brackets which may be coated with metallic or non-metallic materials in such a manner as to reduce friction to thereby further facilitate the sliding movement of an archwire relative to the brackets during patient treatment.

It is also an object of the present invention to enhance the aesthetic appearance of orthodontic brackets by providing orthodontic brackets and/or archwire retainers in the form of slot inserts and/or flanges which may be coated in various colors to promote style depending on patient preferences.

The flexibility of the self-ligating brackets and archwire retainers with their small compact twin design will make them easy to use in the small confines of a patient's mouth which will give the Orthodontist additional treatment options of using ligatures to hold archwires in place in the bracket slots, and these brackets will solve the limitations of current self-ligating brackets.

The small compact flexible archwire retainers attached to both metallic and non-metallic tie wings of the present invention, with and without a coating, will permit Orthodontists to overcome the many challenges they face during treatment and alignment of a patient's teeth and will make the patient's visits to the Orthodontist to have their braces adjusted a much less complicated process and overall more comfortable and quicker, resulting in making the overall treatment experience a more pleasant one while achieving superior results for the patient.

Welding or otherwise attaching the shape memory retainers to the archwire side of the tie wings of metal brackets will create an aesthetic metallic self-ligating bracket. The attachment of shape memory retainers to ceramic or other non-metallic brackets by welding or likewise attaching the shape memory retainers to the occlusal aspects of current steel archwire inserts of ceramic brackets will produce an aesthetic ceramic bracket that is self-ligating. The orthodontist will also be able to attach colorful elastic, elastomeric ties and power chains to these twin self-ligating brackets that are pleasing to the patient.

BRIEF DESCRIPTION OF THE DRAWINGS

A better understanding of the invention will be had with reference to the accompanying drawings wherein.

DESCRIPTION OF THE PREFERRED EMBODIMENTS

Figure 1A:
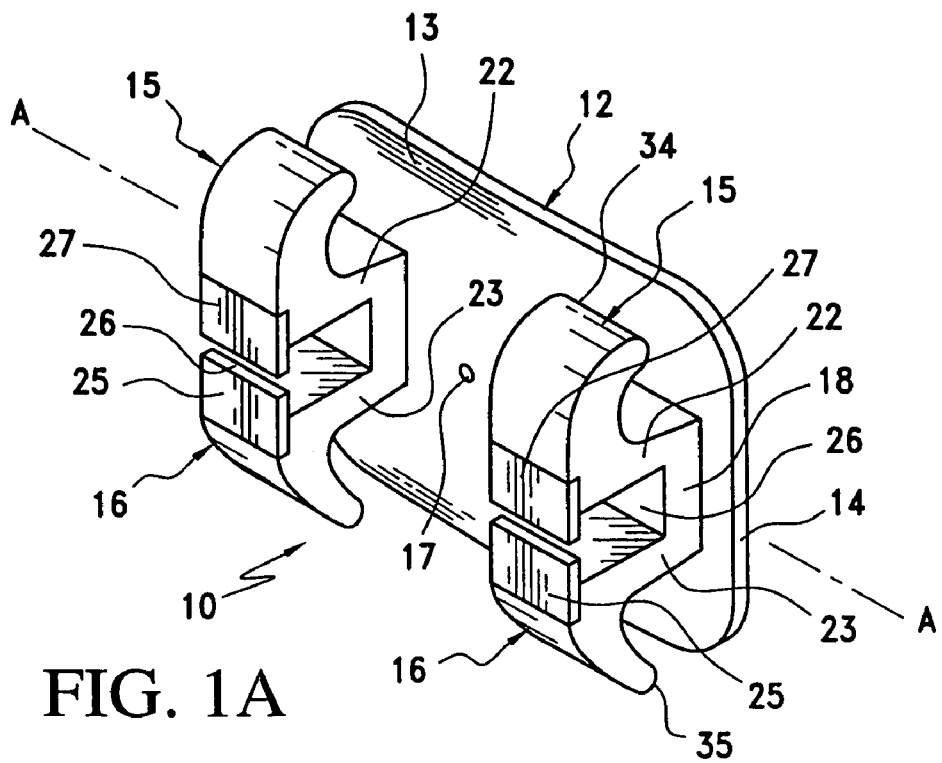
FIG. 1A is a front perspective view of an orthodontic bracket with a first embodiment of an archwire retainer in accordance with the present invention in the form of opposing shape memory flanges.
Figure 1B:
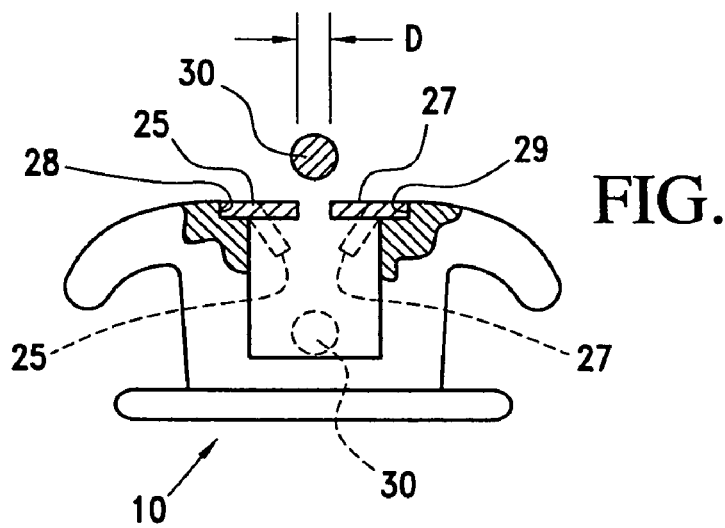
FIG. 1B is a side view of the bracket of FIG. 1A having portions shown in cross section.
Figure 1C:
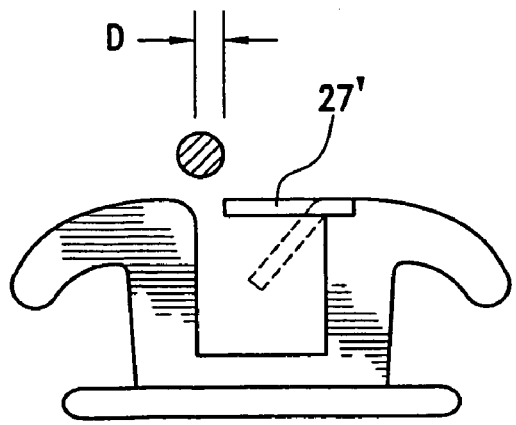
FIG. 1C is a side view of a modification of the bracket shown in FIGS. 1A and 1B.

With continued reference to drawing FIGS. 1A-1C, a first embodiment of orthodontic bracket 10 of the present invention includes a contoured base 12 having a front surface 13 and tooth engaging surface 14. The rear surface 14 is generally slightly concavely contoured so as to match the surface contour of a patient's tooth.

The orthodontic bracket further includes two pair of spaced opposing tie wings 15 and 16 which are shown as being spaced on opposite sides of a central recess 17 which is formed generally centrally of the front surface of the bracket base 12. The recess 17 is used to facilitate alignment of the bracket relative to a patient's tooth using an instrument such as a Boone gauge. As opposed to the recess 17, a linear groove may be provided in the front surface 13 of the bracket base for facilitating alignment, see the embodiment of FIG. 4B at 17B.

Each pair of tie wings includes a base portion 18 from which extend posts 22 and 23. The generally parallel posts 22 and 23 define an archwire guide slot 26 of approximately 0.018 to 0.022 inch therebetween of a size to slidingly receive an archwire, such as shown at 30 in FIG. 1B.

Figure 2A:
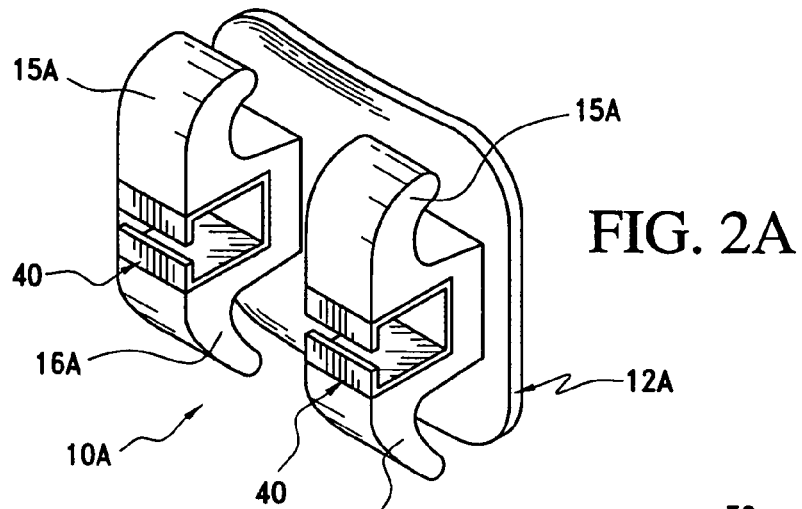
FIG. 2A is a front perspective view of another embodiment of an archwire retainer and an orthodontic bracket according to the invention.

To enable the brackets of the present invention to be self-ligating, a variety of archwire retainers are disclosed which may be welded, adhered or otherwise secured to one or more of each pair of opposing tie wings metal archwire slot, or within the archwire guide slots 26 defined between each pair of opposing tie wings. Each archwire retainer includes at least one flange which is designed to substantially close the opening into the archwire guide slot to thereby prevent removal of an archwire seated with the retainer and/or archwire guide slot. In the embodiment of FIGS. 1A-1C, the retainers are in the form of planar or slightly curved flanges, wherein the embodiment shown in FIGS. 2A and 3C the inserts are generally U-shaped having one or more flanges associated therewith. In the embodiment of FIGS. 4A and 4B, the retainers are generally L-shaped.

In the embodiment of FIGS. 1A-1C, archwire retainers 25 and 27 are shown inserted into grooves or recesses 28 and 29 formed in the upper portion of each tie wing 15 and 16, respectively. One or both of the retainers are formed of a shape memory material and both are in a form of a flange which protrudes toward the opposite tie wing across and opening into the archwire guide slot 26. The flanged retainers may be planar or slightly convex along their upper surfaces. Either one or both of the flanged retainers 25 and 27 may be moved from a predetermined or rest position, as shown in full line in FIG. 1B, to a position as shown in dotted line, to permit insertion or withdrawal of the archwire 30 into the archwire guide slot 26. After passage of the archwire, the flanged retainers recover to their predetermined positions. In their rest or predetermined positions, the opposing tips of the flanged retainers are spaced at a distance "D" relative to one another. The distance "D" is a dimension which is less than a diameter of the archwire and will normally be from 0.010 to 0.012 inch. In some embodiments, the tips of the retainers 25 and 27 may touch, in which case dimension "D" would be zero.

As opposed to having flanged retainers on both tie wings 15 and 16, only one flanged retainer 27' may be provided which is formed of a shape memory material and which functions exactly as described for the flanged retainers 25 and 27, as shown in FIG. 1C.

With specific reference to FIGS. 2A-2D, another embodiment of the invention is shown with, a bracket 10A which is smaller than that of the bracket of FIGS. 1A-1C such that the opposing pairs of tie wings 15A and 16A are more closely spaced. The bracket includes a base 12A and the tie wings define archwire guide slots 26A therebetween.

In the embodiment of FIGS. 2A-2D, U-shape archwire retainers 40 are shown. Each retainer 40 includes a bottom wall 41 and opposing side walls 42 and 43 from which extend inwardly opposing flanges 44 and 45, respectively. The retainers 40 are of a size to be cooperatively seated within the archwire guide slots 26A defined between the tie wings 15A and 16A and are retained therein such as by laser welding. The retainers may be fabricated or secured during bracket manufacture or may be secured within the archwire guide slots by an Orthodontist.

Figure 2B:
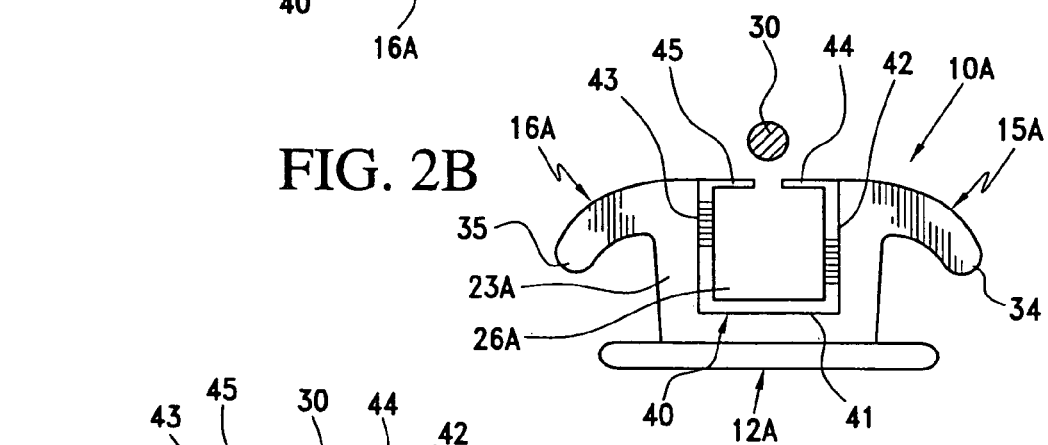
FIG. 2B is a side elevational view of the embodiment of the invention of FIG. 2A showing opposing flanges of an archwire retainer unflexed before insertion of the archwire relative to the archwire guide slot defined between the opposing tie wings.
Figure 2C:
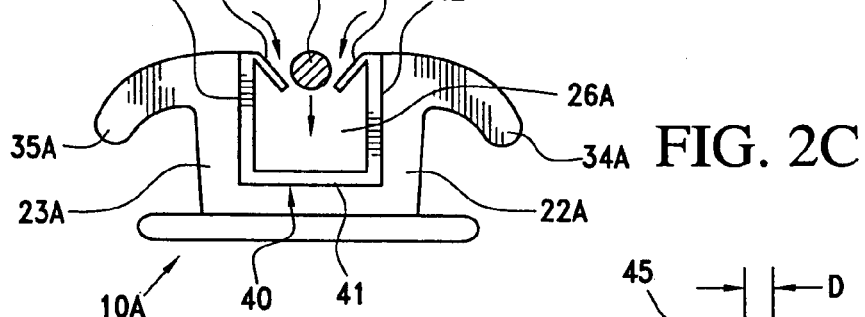
FIG. 2C is a side elevational view of the bracket of FIG. 2A showing the flanges of the archwire retainer flexed to permit insertion of the archwire therebetween.

At least one, and preferably both, of the opposing flanges 44 and 45 are designed to be flexed from a predetermined or rest position, as shown in FIG. 2B, to a position as shown in FIG. 2C to thereby permit insertion or removal of the archwire 30 relative to the archwire guide slot 26A. In this respect, the flanges and/or one or both side walls 42 and 43 and/or the entire retainer 40 is formed of a shape memory material.

Figure 2D:
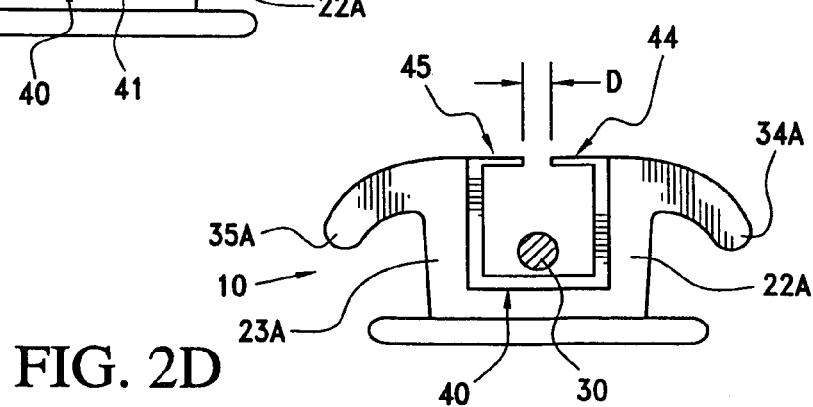
FIG. 2D is a side elevational view of the bracket of FIG. 2A illustrated with an archwire being seated within the archwire guide slot defined between the two opposing tie wings.

Thus, the shape memory archwire retainers of the present invention are self-ligating. That is, the flanges and or other portions of retainer 40 which are formed of the shape memory material, allow the flanges to flex as shown and illustrated in FIG. 2C to permit insertion or removal of the archwire 30. In this respect, the retainers, or portions thereof, are preferably formed of a nickel-titanium material. This material exhibits superelasticity and, therefore, shape memory, such that the flanges may be flexed to separate and permit the insertion or removal of the archwire. Once force is removed, the flanges return to their normal predetermined configuration and position as shown in FIG. 2D. Both shape memory metallic alloys, non-metallic resins, polymers, and other materials that exhibit a shape memory may also be used.

To securely retain an archwire within the archwire guide slot 26A, the opposing flanges 44 and 45 are spaced at a distance "D" of approximately 0.010-0.012 inch which is smaller than the diameter of the archwire. Again, in some embodiments, the flanges may actually touch one another, such that the distance "D" is zero.

The tie wings 15A and 16A further include posts 22A and 23A and outer tie wing flanges 34A and 35A which may be used in a conventional manner to secure archwires with ligature wires and other attachments during patient treatment, as is necessary. In the preferred embodiment, the entire outer surface of the head portion is shown as being generally convex.

Figure 3A:
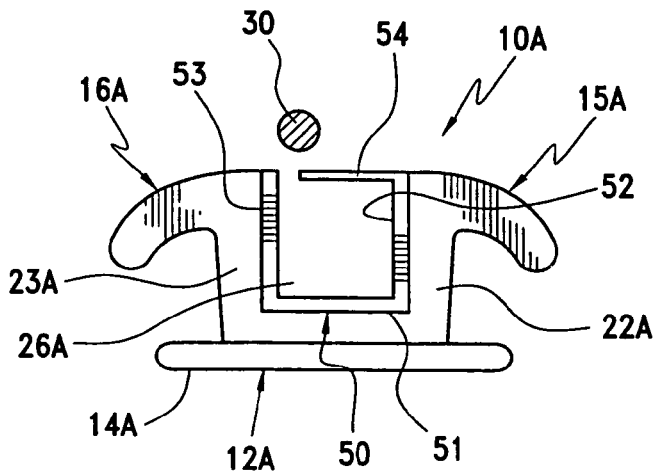
FIG. 3A is a view similar to FIG. 2B showing another embodiment of an archwire retainer.
Figure 3B:
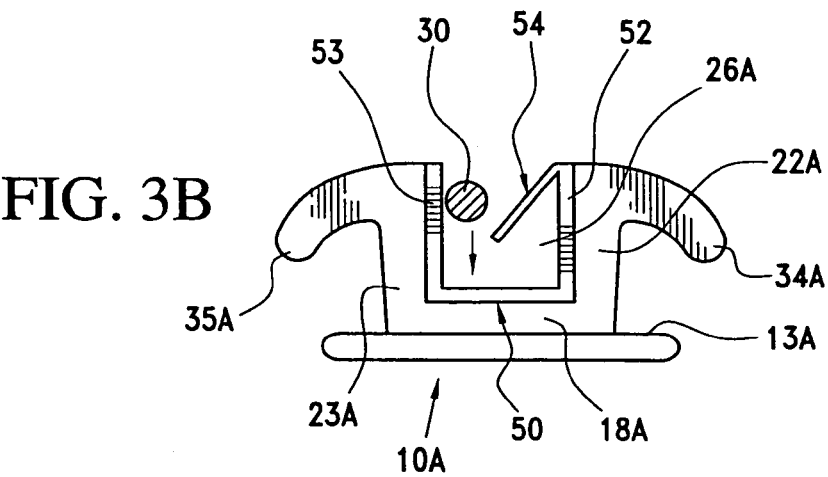
FIG. 3B is a view similar to FIG. 2C except showing the archwire insert of FIG. 3A.
Figure 3C:
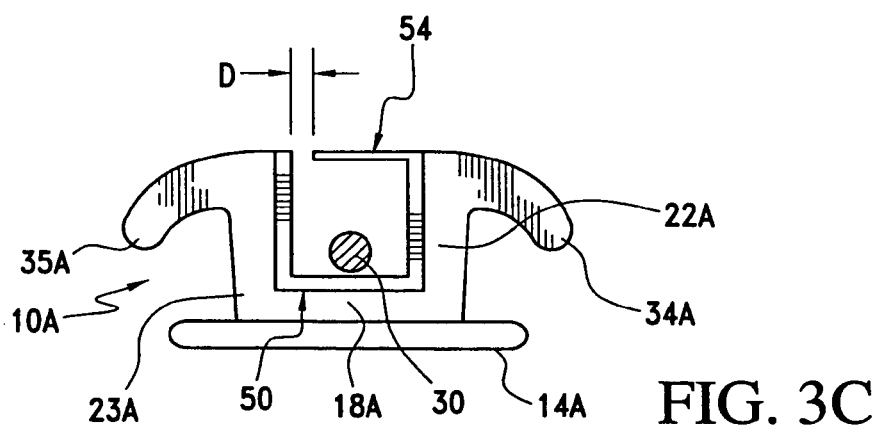
FIG. 3C is a view similar to FIG. 2D except showing the archwire insert of FIG. 3A.
Figure 4A:
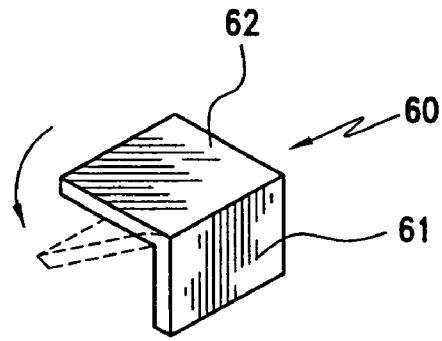
FIG. 4A is a side view of a further embodiment of an archwire retainer of the invention.
Figure 4B:
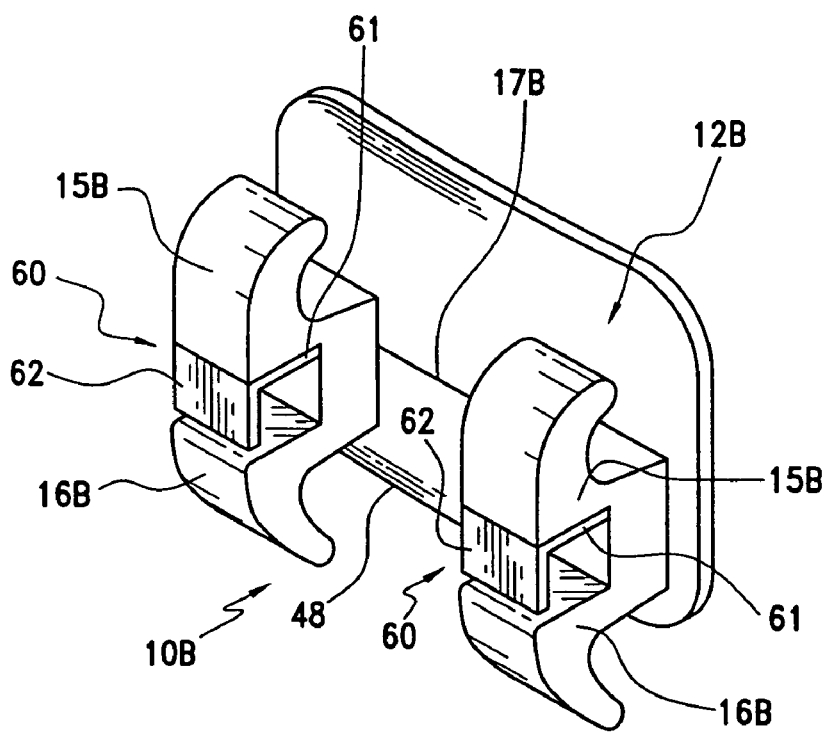
FIG. 4B is a front perspective view of a further embodiment of an archwire retainer and an orthodontic bracket in accordance with the invention.

A varied embodiment of the invention of FIGS. 2A-2D is shown in FIGS. 3A-3C. In this embodiment the generally U-shaped retainers 50 are formed having a bottom wall 51, opposing side walls 52 and 53 and a single retainer flange 54. The insertion of the archwire 30 is illustrated in FIG. 3B. The retainers 50 are formed of the same shape memory materials as defined with respect to the previous embodiment.

As opposed to each tie wing including a base portion, such as illustrated at 18A, it is possible that the tie wings 15A and 16A are formed such that the posts 22A and 23A extend upwardly from the front surface 13A of the bracket base 12A. In such instances, the archwire retainer may be elongated so as to be seated within the archwire guide slots defined between both pair of opposing tie wings. Such a retainer is shown in FIGS. 5, 6A and 6B.

Figure 5:
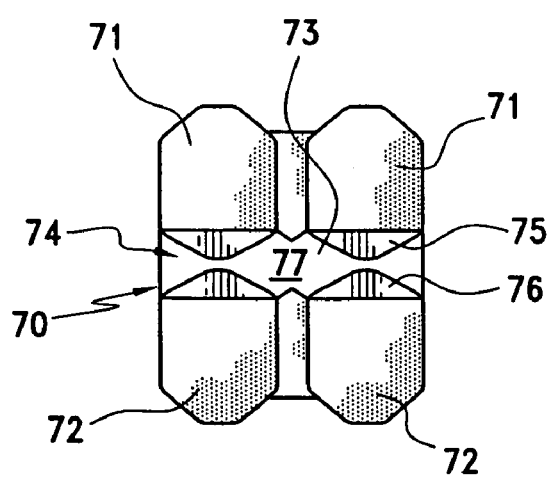
FIG. 5 is a top plan view of yet another embodiment of an archwire insert for a ceramic orthodontic bracket in accordance with the invention.

In FIG. 5 a self-ligating ceramic bracket 70 is shown with ceramic tie wings 71 and 72. The archwire guide slot 73 is formed by a metal insert (not shown) in which retainer 74 is secured. The retainer 74 includes archwire retainer flanges 75 and 76 that may be formed of a shape memory metallic material, non-metallic material, resins, polymers and other materials. The shape memory flanges 75 and 76 extend inwardly from sidewalls (not shown) which, with bottom wall 77, form a U-shape. The flanges 75 and 76 flex to separate and permit the insertion and removal of an archwire relative to the archwire guide slot. One force is removed, the flanges return to their normal predetermined configuration and position as shown in FIG. 5.

Figure 6A:
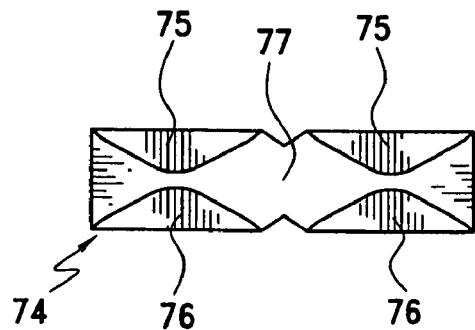
FIG. 6A is a top plan view of the archwire retainer of FIG. 5.
Figure 6B:
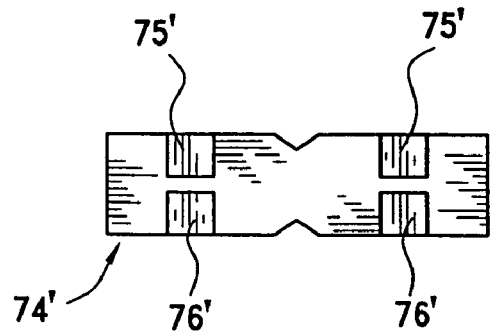
FIG. 6B is a top plan view of a modified archwire retainer similar to FIG. 6A.

The archwire retainers 74 formed of shape memory metallic and/or non-metallic material are better shown in FIG. 6A. The elongated shape memory archwire retainer 74 as rounded flanges 75 and 76. As shown in FIG. 6B, a retainer 74' may be formed having rectangular flanges 75' and 76'.

Figure 7A:
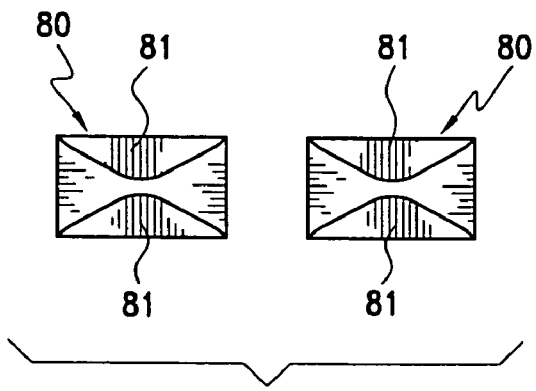
FIG. 7A is a top plan view of a further embodiment of the invention showing two short shape memory archwire retainers in accordance with the invention.
Figure 7B:
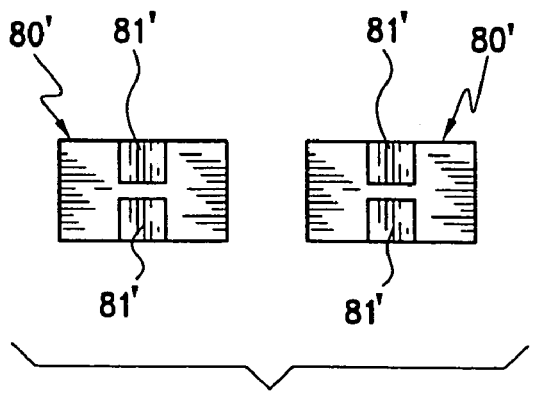
FIG. 7B is a view similar to FIG. 7A showing two modified short archwire retainers.

With reference to FIG. 7A, two short U-shaped retainers 80 are shown which are also formed of shape memory metallic and/or non-metallic material. The two shorter shape memory archwire retainers have rounded flanges 81. Two short retainers 80' may be formed having rectangular flanges 81' as shown in FIG. 7B. The retainers 80 and 80' fit into the archwire guide slots and are attached to the inner archwire side of the tie wings or to a steel archwire slot liner such that they flex to separate and permit the insertion and removal of an archwire relative to the archwire guide slot and then return to their original configuration and position.

With specific references to FIGS. 4A and 4B, another embodiment of retainer 60 is shown which may be secured to a bracket such as the brackets 10 and 10A shown in FIGS. 1A-3C. In this embodiment, the retainer is generally L-shaped having a leg 61 which is designed to be welded, adhered or otherwise secured to one of the posts of the tie wings. A flange 62 extends from the leg 61 and serves to retain an archwire within the archwire guide slot. At least the flange 62 is formed of the same shape memory material, as previously described, such that the flange may be flexed, as shown in dotted line, to permit insertion or removal of an archwire, afterwhich, the flange will return to its predetermined position, as shown in full line.

As the present invention utilizes archwire retainers formed of a nickel-titanium or other material exhibiting shape memory, the flanges or other portions of the retainers exhibit some degree of flexibility. As noted, the flexible retainers may be welded or otherwise attached to the archwire side of metal tie wings of metal brackets or likewise attached to current steel archwire inserts associated with ceramic brackets. The shape memory retainers may also be inserted into archwire guide slots of other non-metallic brackets.

With the structure of the present invention, it is possible to apply the bracket to extremely twisted or crooked teeth wherein only two tie wings may be appropriately aligned with the tooth to receive an archwire. During initial treatment, the archwire may be seated within a single archwire guide slot defined by one pair of opposing tie wings until such a time as a tooth can be moved to a position wherein the archwire may be aligned within both pair of tie wings and seated into the bracket archwire guide slots. In this respect, it should be noted that tie wings of the present invention define archwire guide slots which are preferably axially aligned relative to one another along a line A-A as shown in FIG. 1.

With reference to FIG. 4B, another embodiment of the invention is shown. In this embodiment, the bracket 10B has archwire retainers 60, as previously described, with flanges 62 formed of the same shape memory material as previously described. The bracket has two pair of opposing tie wings 15B and 16B which extend from a base 12B. However, the tie wings extend upwardly from a position more closely spaced to a gingival edge 48 of the bracket base. This structure permits correct bonding of brackets on short or gingivally displaced teeth. In this embodiment, a horizontal recess alignment guide 17B is shown, as opposed to the recess 17 shown in FIG. 1. Any of the archwire retainers of the invention may be used with the bracket 10B. The provision of the bracket tie wings extending upward from a position close to a gingival edge of the bracket base may also be used in the embodiments of the invention shown in FIGS. 1A-C, 2A-D, 3A-C, 4A and 5.

Due to the shape memory material from which the retainers of the present invention are formed, very low friction surfaces are presented for guidingly engaging the archwire. The lower friction between the bracket and the archwire, the more smoothly and easily the archwire will function to move a patient's tooth to a desired position, thus facilitating patient treatment. In this respect, the present invention also provides for further decreasing the frictional surface resistance of the brackets, and retainer by allowing the brackets and/or archwire retainers to be coated with other materials. By way of example, except the bonding base pad or mesh of the bracket, the surface of the brackets including the tie wings and base, especially in the area of the archwire guide slots, and/or the retainers may be plated or electroplated with metallic elements such as nickel, gold, copper, or silver. As opposed to a plating with metallic material, the brackets, except the bonding base pad or mesh may be coated with different plastics including polytetrafluoroethylene (PTFE) including Teflon™, thermosetting polymers or other polymers, with or without coupling agents which are specifically provided to create a smoother surface and thereby reduce friction.

In accordance with the invention, the surface treatments may also include coloring agents. It may be desired to increase the aesthetic appearance of new orthodontic brackets and/or archwire retainers by including coloring agents which would present hues of gold, tooth color, red, green, blue or other colors.

To facilitate the coating process, the surface of the orthodontic bracket and/or archwire retainer and the tie wings may be chemically etched or mechanically pitted such as by blasting to create a surface roughness to facilitate bonding of a coating material.

The orthodontic brackets of the present invention are preferably used with archwires which are also formed of a nickel-titanium material, such as Nitinol™, which is a superelastic metallic material which exhibits flexibility and has a shape memory.

The flexibility of the nickel-titanium, or other material exhibiting shape memory, self-ligating brackets and archwire retainers of the present invention and the small compact twin tie wing design of the invention make it easy for the brackets to be used in particularly difficult areas and small confines within the patient's mouth and may be used with or without the need for conventional plastic or metal ligatures to hold the archwire in place during patient treatment. Additionally, elastomeric colors, elastomeric ties, elastomeric power chains directional elastics or various attachments may be added to the bracket to facilitate a smooth orthodontic treatment. The present invention promotes patient treatment by further facilitating the mechanical movement between the archwire and the orthodontic brackets which will reduce patient treatment time and therefore increase patient comfort.

The foregoing description of the preferred embodiment of the invention has been presented to illustrate the principles of the invention and not to limit the invention to the particular embodiment illustrated. It is intended that the scope of the invention be defined by all of the embodiments encompassed within the following claims and their equivalents.

I claim:

1. A self-ligating orthodontic bracket comprising: a base having front and rear surfaces, two pair of spaced opposing tie wings, each tie wing having a post member extending from said front surface of said base in spaced relationship with respect to a post member of an opposing tie wing, each pair of opposing tie wing post members define an archwire guide slot therebetween of a first dimension to slidingly receive an archwire therein, each pair of opposing tie wings including head portions and at least one archwire retainer flange formed as a portion of a generally U-shaped archwire retainer having opposing side walls and being seated between opposing tie wing post members in said archwire guide slot therebetween, said at least one archwire retainer flange being of a size to be seated in a single archwire guide slot between one of said two pair of tie wings, said archwire retainer flange extending from one of said side walls of said archwire retainer so that said archwire retainer flange does not extend into said head portions of said tie wings, said archwire retainer flange extending from at least one of said tie wings in a predetermined position relative to said archwire guide slot to retain an archwire within said archwire guide slot, said archwire retainer flange having an arcuate surface for contacting said archwire as said archwire is slidingly received in said archwire guide slot, and said at least one archwire retainer flange being formed of a material such that said at least one archwire retainer flange exhibits flexibility and shape memory effect allowing said at least one archwire retainer flange to move relative to said archwire guide slot to permit insertion or removal of an archwire relative to said archwire guide slots afterwhich said at least one archwire retainer flange returns to its predetermined position, said arcuate surface being arcuate in a plane generally parallel to said base.

2. The self-ligating orthodontic bracket of claim 1 wherein said material is a nickel-titanium material.

3. The self-ligating orthodontic bracket of claim 1 wherein said at least one archwire retainer flange extends from a leg member secured to one of said tie wing posts.

4. The self-ligating orthodontic bracket of claim 1 including opposing archwire retainer flanges extending from each of said side walls of said archwire retainer, and said opposing archwire retainer flanges being positioned relative to one another to prevent the unplanned removal of the archwire from said archwire guide slots.

5. The self-ligating orthodontic bracket of claim 1 in which said two pair of opposing tie wings are aligned with one another and spaced adjacent a gingival edge of said base of said bracket.

6. The self-ligating orthodontic bracket of claim 1 wherein said archwire retainer is of a size to be cooperatively seated with the said archwire guide slots between both pair of tie wings.

7. The self-ligating orthodontic bracket of claim 1 wherein said at least one archwire retainer flange is welded or adhered to a recess formed in said at least one tie wing.

8. The self-ligating orthodontic bracket of claim 1 in which said at least one archwire retainer flange is coated with a coating material selected from a group of materials consisting of metallic materials, non-metallic materials, and polymers.

9. The self-ligating orthodontic bracket of claim 8 wherein said polymers are thermosetting polymers.

10. The self-ligating orthodontic bracket of claim 8 in which said coating material includes a coloring agent.

11. The self-ligating orthodontic bracket of claim 8 wherein said coating material is a material applied by electroplating.

12. The self-ligating orthodontic bracket of claim 1 in which at least one, portion of said archwire retainer is coated with a coating material selected from a group of materials exhibiting a low coefficient of friction consisting of metallic materials, and non-metallic materials, and polymers.

13. The self-ligating orthodontic bracket of claim 12 wherein said non-metallic polymers are thermosetting polymers.

14. The self-ligating orthodontic bracket of claim 12 in which said coating material includes a coloring agent.

15. The self-ligating orthodontic bracket of claim 1 wherein said material is selected from a group of materials exhibiting shape memory consisting of metallic materials and non-metallic materials.

16. The self-ligating orthodontic bracket of claim 1 in which said at least one archwire retainer flange is coated with a coating material selected from a group of materials consisting of metallic materials, non-metallic materials, and polymers.

17. The self-ligating orthodontic bracket of claim 1 in which said two pair of opposing tie wings are aligned with one another and spaced adjacent a gingival edge of said base of said bracket.

18. The self-ligating orthodontic bracket of claim 1 in which said at least one archwire retainer flange is secured to a metal archwire insert of a ceramic bracket.

* * * * *